United States Patent [19]
Duffey

[11] Patent Number: 5,114,670
[45] Date of Patent: May 19, 1992

[54] PROCESS FOR STERILIZING SURFACES

[75] Inventor: Craig L. Duffey, Galena, Ohio

[73] Assignee: Liqui-Box/B-Bar-B Corporation, Worthington, Ohio

[21] Appl. No.: 575,361

[22] Filed: Aug. 30, 1990

[51] Int. Cl.$^5$ .............................................. A61L 2/18
[52] U.S. Cl. ..................................... 422/24; 422/34; 422/28; 422/292; 422/304
[58] Field of Search .................. 422/23, 24, 34, 28, 422/292, 304

[56] References Cited

U.S. PATENT DOCUMENTS

| | | |
|---|---|---|
| Re. 33,007 | 8/1989 | Bier . |
| 4,169,123 | 9/1979 | Moore et al. . |
| 4,169,124 | 9/1979 | Forstrom et al. . |
| 4,230,663 | 10/1980 | Forstrom et al. . |
| 4,366,125 | 12/1982 | Kodera et al. . |
| 4,642,165 | 2/1987 | Bier . |
| 4,648,978 | 3/1987 | Makinen et al. . |
| 4,744,951 | 5/1988 | Cummings et al. . |
| 4,797,255 | 1/1989 | Hatanaka et al. ........................ 422/28 |
| 4,843,867 | 7/1989 | Cummings . |
| 4,863,688 | 9/1989 | Schmidt et al. . |

FOREIGN PATENT DOCUMENTS

| | | |
|---|---|---|
| 1196764 | 11/1985 | Canada ............................... 422/24 |
| 2144543 | 3/1973 | Fed. Rep. of Germany . |
| 1513266 | 5/1984 | United Kingdom . |

OTHER PUBLICATIONS

"The Combined Effect of Hydrogen Peroxide and Ultraviolet Irradiation on Bacterial Spores"; Journal of Applied Bacteriology; vol. 47, pp. 263-269; 1979.

"Vapor Phase Hydroen Peroxide Sterilization"; American Sterilizer Company; R. K. O'Leary et al.

Primary Examiner—Jill A. Johnston
Assistant Examiner—Lyle A. Alexander
Attorney, Agent, or Firm—Vorys, Sater, Seymour & Pease

[57] ABSTRACT

A process is disclosed for sterilizing surfaces utilizing hydrogen peroxide gas in combination with preselected ultraviolet energy.

6 Claims, 1 Drawing Sheet

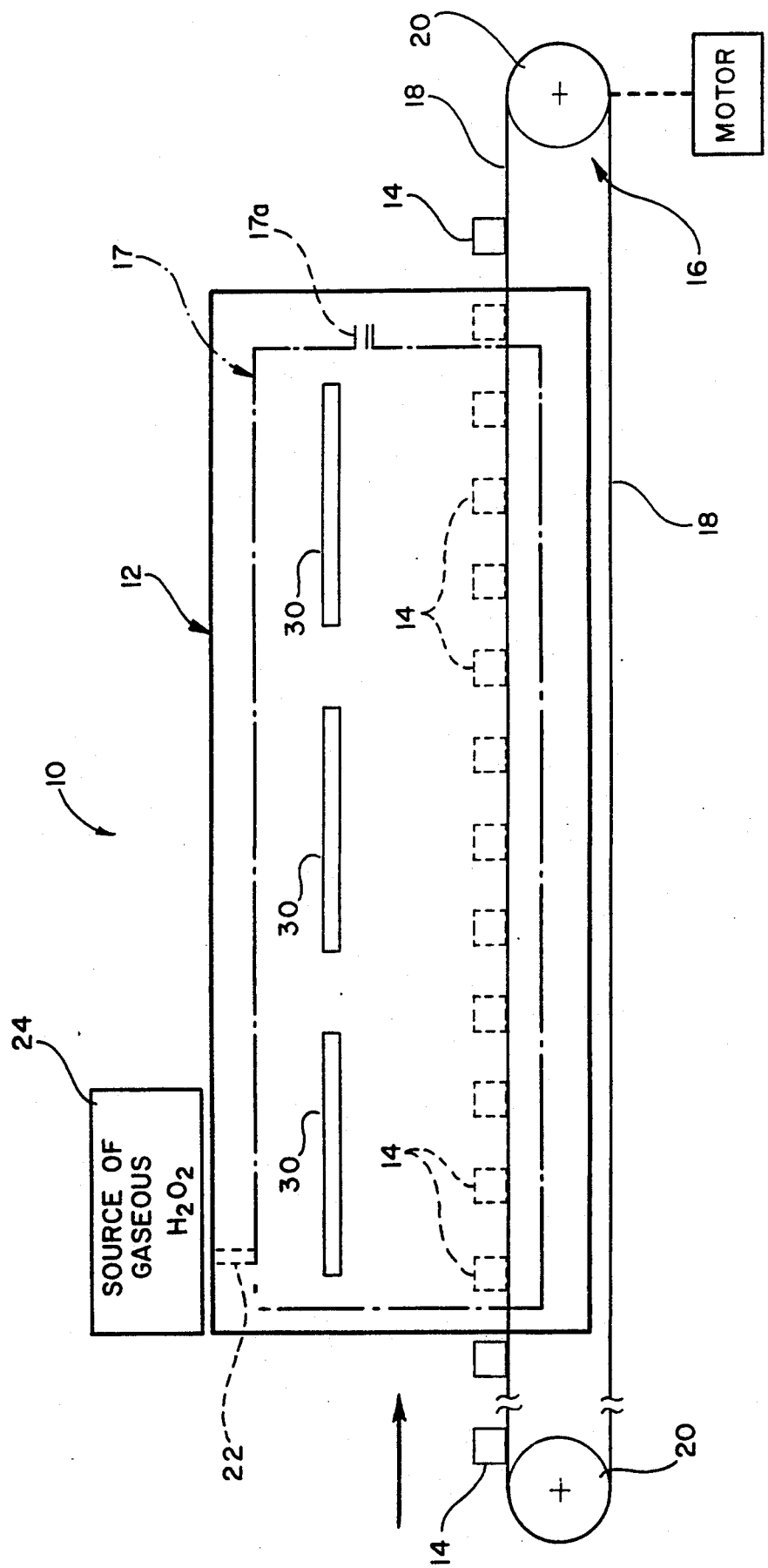

PROCESS FOR STERILIZING SURFACES

BACKGROUND OF THE INVENTION

The present invention relates generally to a process and apparatus for effecting sterilization of objects and, more particularly, to a process and apparatus for effecting sterilization through the utilization of hydroxide peroxide and ultraviolet energy.

In the field of sterilization, liquid hydrogen peroxide has been used effectively as a bactericide. There are numerous applications of liquid hydrogen peroxide for accomplishing sterilization and disinfection purposes. One is described in British Pat. No. 1,513,266, in which hydrogen peroxide ($H_2O_2$) with steam are mixed together, and the resulting mixture is condensed on the inner wall of an enclosure. The condensate is eventually evacuated, the enclosure is dried and sterilization is thereby achieved. Another approach is described in U.S. Pat. No. 4,366,125, which discloses using an atmospheric mist or fog of liquid phase hydrogen peroxide and followed by irradiation with ultraviolet energy. Still another sterilization approach is to utilize gaseous phase hydrogen peroxide. Gaseous phase hydrogen peroxide is an effective sterilant which is employed for use in sterilizing objects. Examples of such prior art approaches are described adequately in U.S. Pat. Nos. 4,169,123 and 4,169,124. Basically, in such a procedure, hydrogen peroxide vapor is used for sterilization purposes and is achieved by vaporizing, in a closed sterilization chamber, a relatively dilute liquid solution of hydrogen peroxide and water. The vapors so produced contact the items to be sterilized. This technique is generally referred to as cold gas sterilization as opposed to a heat or liquid contact sterilization. Vaporous hydrogen peroxide because of its low toxicity is desireable since it provides a safe alternate for sterilizing hard surfaces.

It is also known to use ultraviolet energy provided by a ultraviolet lamp for purposes of effecting sterilization of various types of articles. Generally, relatively long sterilization times are required when using ultraviolet energy. One known approach, described in an article entitled, "The Combined Effect of Hydrogen Peroxide and Ultraviolet Irradiation on Bacterial Spores", appearing in *Journal of Applied Bacteriology*, Vol. 47, 263-269, 1979, and has described combining hydrogen peroxide with ultraviolet energy. However, in this latter approach, the hydrogen peroxide utilized was in a liquid phase. Also, U.S. Pat. No. 4,366,125 describes utilization of ultraviolet radiation with an atmospheric mist or fog of finely divided hydrogen peroxide liquid, but at separate times.

SUMMARY OF THE INVENTION

According to the present invention, there is provided an improved process for effecting sterilization of a surface. Included in the process is the step of providing a gaseous hydrogen peroxide medium; introducing the gaseous hydrogen peroxide into a sterilization chamber; applying predetermined amounts of ultraviolet energy to the surface to be sterilized for effecting sterilization of the surface.

In an illustrated embodiment, the ultraviolet energy has a wavelength frequency in a range of from about 180 nm to 280 nm.

In another illustrated embodiment, the ultraviolet energy is applied for a period of from about 20 sec. to 40 sec.

In accordance with the present invention, there is provided an apparatus for use in sterilizing at least a surface of an article. Included in the apparatus is a sterilization assembly having a sterilization chamber. The sterilization chamber assembly includes inlet and outlet means which allow the introduction and removal of articles to and from the sterilization chamber. Included is means for introducing a gaseous hydrogen peroxide sterilant into the sterilization chamber. Provision is made for means for simultaneously irradiating the chamber and the surface with ultraviolet energy. The combination of the ultraviolet energy and the hydrogen peroxide vapor provides a synergistic effect for purposes of sterilizing and disinfecting the article to be sterilized.

In an illustrated embodiment, the means for irradiating the article with ultraviolet energy includes an ultraviolet lamp which is operable to produce a preselected wavelength of ultraviolet energy for predetermined periods of time.

In an illustrated embodiment, the ultraviolet energy is applied at all times while the hydrogen peroxide is present. The time of exposure is determined by how long the article is in the sterilization chamber, for example, the filler speed associated with the filling of expandable bags.

Among the other objects and features of the present invention are the provision of an improved apparatus and process for sterilizing a surface; the provision of an improved process and apparatus for sterilizing a surface through the utilization of gaseous phase hydrogen peroxide and ultraviolet energy, whereby a synergistic sterilizing effect occurs; and the provision of an improved process and apparatus of the last noted type wherein the gaseous phase hydrogen peroxide and ultraviolet energy are applied substantially simultaneously to the surface.

Still other objects and further scope of applicability of the present invention will become apparent from the detailed description to follow when taken in conjunction with the accompanying drawings in which like parts are designated by like reference numerals throughout the several views.

BRIEF DESCRIPTION OF THE DRAWING

The sole drawing figure is a schematic elevational view showing various components forming an apparatus embodying the principles of the present invention.

DETAILED DESCRIPTION

Reference is made to the sole figure for illustrating a preferred embodiment of a sterilization apparatus 10 incorporating the principles of this invention and which is useful for effecting sterilization of articles, such as dispensing spouts for use on containers for dispensing beverages. Of course, the present invention contemplates that the process and apparatus can be used for sterilizing a variety of different surfaces and objects.

As depicted, there is a sterilization apparatus 10 which defines an enclosed sterilization chamber assembly 12. The sterilization chamber assembly 12 includes inlet and outlet door mechanisms (not shown) which are openable and automatically closeable upon the movement therethrough of articles 14 to be sterilized. Associated with the sterilization apparatus 10 is a conveyor assembly 16 which carries the articles 14 through the sterilization apparatus 10. The sterilization apparatus 10 is provided with a sterilization chamber 17 having an evacuation outlet 17a. The evacuation outlet 17a is connected to suitable negative source of pressure (not shown) for purposes of evacuating the gaseous sterilant from the sterilization chamber 17. In this manner, there is a continuous flow of vapor phase hydrogen peroxide through the sterilization chamber. The conveyor assembly 16 includes a conveyor belt 18 which is trained over a pair of suitable driving and driven rollers 20. It will be appreciated that the articles 14 will be placed on the top flight of the conveyor belt 18 and travel through the sterilization chamber 17 in the direction of the arrow. Although a conveyor is used for transporting, other types of conveying systems may be employed within the spirit and scope of the invention. Also, a batch type apparatus can be used. The sterilization chamber 17 is insulated to maintain heat.

The chamber 17 is in fluid communication, by means of a conduit 22, with a suitable source 24 of heated gaseous or vapor phase hydrogen peroxide. The gaseous hydrogen peroxide source 24 is a commercial unit. The gaseous sterilant source 24 is defined by an apparatus which can function as described generally in U.S. Pat. No. 4,863,688. Since the apparatus for the formation of the vapor phase hydrogen peroxide does not, per se, form an aspect of this invention, the last-noted patent is incorporated herein by reference for purposes of describing such an apparatus. Gaseous hydrogen peroxide is highly effective for sterilizing or decontaminating surfaces. The hydrogen peroxide, in the vapor state, can have its concentration vary of from about 29% to 35%. By increasing the concentration, the ability to kill microorganisms within a given contact period will increase accordingly. The higher the concentration, for example above 29%, the higher the ability to kill spore and non-spore types of microorganisms. The degree of concentration of the hydrogen peroxide does not affect the efficiency of the treatment of the present invention other than would be expected by varying the concentration.

Heaters (not shown) located prior to the chamber are used to heat the articles. They are intended to heat the articles being treated in the chamber so that the temperature differentials between the article 14 and the hydrogen peroxide gas do not become so great that they result in condensation. Condensation results in the hydrogen peroxide returning to the liquid phase which is less efficient. The preferred temperature for the articles is 110° F. whereas the gaseous hydrogen peroxide enters the sterilizing chamber at approximately 140° F. The articles can be heated to a preselected temperature range of from about 1OO° F. to 120° F. The gas temperature is the result of the hydrogen peroxide vapor generation and is not subsequently heated. It does, however, remain constant as a result of the controlled parameters of generation.

In this embodiment, there is provided a plurality of ultraviolet (UV) ray lamps 30 which are effective to irradiate the hydrogen peroxide gas in the enclosed sterilizing chamber 17 and the articles 14 with preselected amounts of ultraviolet energy. In a preferred embodiment, ultraviolet energy is supplied within a wavelength frequency range of from about 200 nm to 280 nm with 254 nm being preferred. Such a wavelength range is referred to as being a germicidal range. The duration of the irradiation step herein is from about 20 sec. to 35 sec., with 35 sec. being preferred. Other ranges consistent with the scope of this invention are contemplated. For instance, the duration is determined by the duration of the articles in the chamber.

The theory of why there is an enhanced sterilizing effect through the utilization of gaseous hydrogen peroxide coupled with irradiation by ultraviolet radiation is not completely understood. However, it is believed that the ultraviolet radiation more effectively interacts with hydrogen peroxide vapor than with liquid hydrogen peroxide or a mist of hydrogen peroxide so as to even more quickly and effectively sterilize the surfaces of the articles being treated. This may, in part, be attributed to the fact that ultraviolet light further accelerates the production of hydroxyl radicals which are effective to kill spores and non-spores. The following sets forth examples of how efficacious the combination of gaseous hydrogen peroxide and ultraviolet energy can be in effecting sterilization.

Sterilization can be measured by the degree to which microorganisms are killed in a given contact period. The contact period for log 6 reduction of both spore type and non-spore type microorganisms when using the method of the present invention is about 6 sec. when the gas temperature is 140° F., the hydrogen peroxide concentration is 9.2 mg/L, and the ultraviolet energy is 25,000 uW/cm$^2$. This compares favorably to a contact period of 12 sec. for use of vapor hydrogen peroxide alone. It has been determined that the contact period for killing spore type and non-spore type microorganisms is reduced by about 50% when using gaseous hydrogen peroxide gas in combination with ultraviolet energy, when compared to the contact period using gaseous hydrogen peroxide alone. Accordingly, the number of objects being sterilized in a given period of time can be increased.

According to the present invention, it will be recognized that certain changes may be made in the above described sterilization process and apparatus without departing from the scope of the present invention herein involved. It is maintained that all matter contained in this description shall be interpreted as illustrative and not in a limiting sense.

I claim:

1. A process for sterilizing a surface of an article comprising the steps of:
   providing a sterilization chamber to sterilize at least a surface of an article;
   introducing a gaseous hydrogen peroxide sterilant into the sterilization chamber substantially free of hydrogen peroxide in liquid phase;
   irradiating the sterilant surface of the article in the sterilization chamber with ultraviolet radiation in an amount to achieve sterilization of the surface; and
   said irradiating step occurs simultaneously with the gaseous hydrogen peroxide being in said sterilization chamber.

2. The process of claim 1, wherein said introducing step introduces heated hydrogen peroxide in the sterilization chamber.

3. The process of claim 2, wherein said heated hydrogen peroxide gas is heated to a temperature in range of from about 135° F. to 145° F.

4. The process of claim 3, wherein said ultraviolet radiation has a wavelength in the range of from about 200 nm to 280 nm.

5. The process of claim 4, wherein said ultraviolet radiation is provided at wavelengths of 254 nm.

6. The process of claim 5, wherein said means for irradiating with ultraviolet energy is operable for a time period of from about 20 sec. to 35 sec.

* * * * *